United States Patent
Klamt

(10) Patent No.: US 11,562,636 B2
(45) Date of Patent: Jan. 24, 2023

(54) CHILD SAFETY SEAT CHECKING SYSTEM, AND CHILD SAFETY SEAT CHECKING METHOD

(71) Applicant: CYBEX GmbH, Bayreuth (DE)

(72) Inventor: Solveig Klamt, Bayreuth (DE)

(73) Assignee: CYBEX GmbH, Bayreuth (DE)

( * ) Notice: Subject to any disclaimer, the term of this patent is extended or adjusted under 35 U.S.C. 154(b) by 183 days.

(21) Appl. No.: 15/733,057

(22) PCT Filed: Nov. 2, 2018

(86) PCT No.: PCT/EP2018/079993
§ 371 (c)(1),
(2) Date: May 1, 2020

(87) PCT Pub. No.: WO2019/086599
PCT Pub. Date: May 9, 2019

(65) Prior Publication Data
US 2021/0056827 A1    Feb. 25, 2021

(30) Foreign Application Priority Data
Nov. 3, 2017   (DE) ..................... 20 2017 106 647.9

(51) Int. Cl.
*G08B 21/02* (2006.01)
*A61B 5/024* (2006.01)
(Continued)

(52) U.S. Cl.
CPC .......... *G08B 21/0205* (2013.01); *A61B 5/024* (2013.01); *A61B 5/0816* (2013.01);
(Continued)

(58) Field of Classification Search
CPC .... G08B 21/0205; G08B 21/24; G08B 21/22; A61B 5/024; A61B 5/0816; A61B 5/4809;
(Continued)

(56) References Cited

U.S. PATENT DOCUMENTS 6,922,147 B1 * 7/2005 Viksnins ............ G08B 21/0208
340/522
8,058,983 B1   11/2011 Davisson et al.
(Continued)

FOREIGN PATENT DOCUMENTS

CN    204814344 U    12/2015
CN    105691294 A    6/2016
(Continued)

OTHER PUBLICATIONS

"International Application PCT/EP2018/079993, International Search Report and Written Opinion dated Feb. 1, 2019", (Feb. 1, 2019), 20 pgs.
(Continued)

*Primary Examiner* — Ryan W Sherwin
(74) *Attorney, Agent, or Firm* — Schwegman Lundberg & Woessner, P.A.

(57) ABSTRACT

A child safety seat checking system for a child safety seat of a vehicle, in particular a motor vehicle, is comprised of at least one child safety seat, a first checking device for checking whether a child is located in the child safety seat, and a second checking device for checking whether a person supervising the child is present, wherein the second checking device is designed to operate in an at least partly portable manner in an operating state of the child safety seat checking system and/or is designed to operate regardless of an on/off state of the vehicle.

16 Claims, 1 Drawing Sheet

Figure 1:
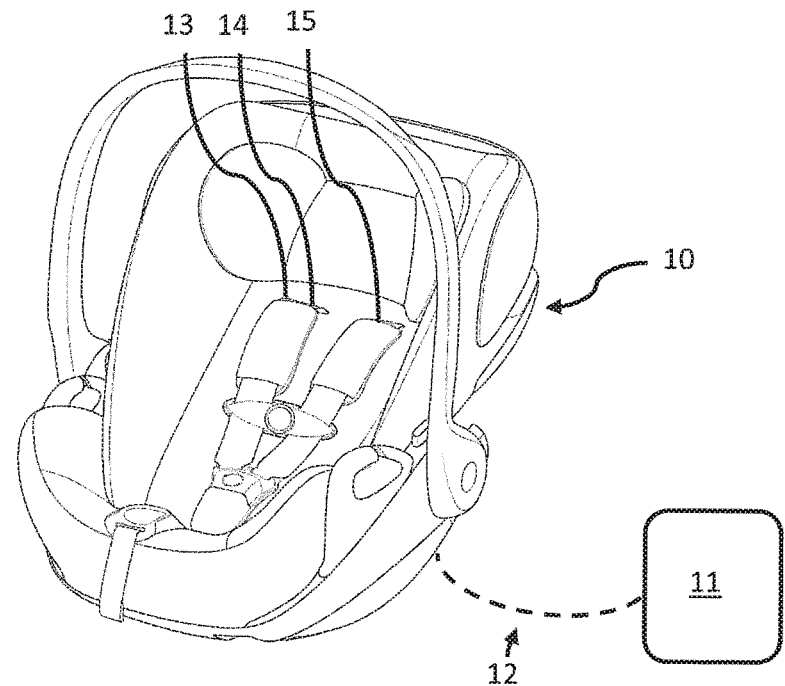

(51) Int. Cl.
*A61B 5/08* (2006.01)
*A61B 5/00* (2006.01)
*G01G 19/50* (2006.01)
*G01G 19/52* (2006.01)
*G01K 13/00* (2021.01)
*G01P 13/00* (2006.01)

(52) U.S. Cl.
CPC .......... *A61B 5/4809* (2013.01); *A61B 5/6891* (2013.01); *G01G 19/50* (2013.01); *G01G 19/52* (2013.01); *G01K 13/00* (2013.01); *G01P 13/00* (2013.01); *A61B 2503/04* (2013.01); *A61B 2503/06* (2013.01); *A61B 2560/0247* (2013.01); *A61B 2560/0252* (2013.01)

(58) Field of Classification Search
CPC .............. A61B 5/6891; A61B 2503/04; A61B 2503/06; A61B 2560/0247; A61B 2560/0252; G01G 19/50; G01G 19/52; G01K 13/00; G01P 13/00; B60N 2/28; B60N 2002/2815; B60N 2/002
See application file for complete search history.

(56) References Cited

U.S. PATENT DOCUMENTS

| | | | |
|---|---|---|---|
| 8,892,302 B1* | 11/2014 | McDonald | G08B 21/22 |
| | | | 701/36 |
| 9,845,050 B1* | 12/2017 | Garza | H04W 4/38 |
| 2004/0160320 A1 | 8/2004 | Edwards et al. | |
| 2011/0241867 A1 | 10/2011 | Neal | |
| 2014/0184404 A1 | 7/2014 | Schoenberg et al. | |
| 2014/0265480 A1* | 9/2014 | Perrin | B60N 2/26 |
| | | | 297/217.4 |
| 2014/0306838 A1* | 10/2014 | Beumler | B60N 2/002 |
| | | | 340/988 |
| 2015/0266395 A1* | 9/2015 | Bradley | B60N 2/002 |
| | | | 701/1 |
| 2016/0379466 A1 | 12/2016 | Payant et al. | |
| 2017/0021800 A1 | 1/2017 | Seibert | |
| 2017/0084153 A1* | 3/2017 | Wolfram | G08B 21/22 |
| 2017/0247015 A1* | 8/2017 | Davis | G08B 21/0225 |
| 2017/0282791 A1 | 10/2017 | Voorhies | |
| 2018/0126950 A1* | 5/2018 | Aiderman | B60R 25/31 |
| 2018/0268679 A1* | 9/2018 | Shropshire | G08B 21/22 |
| 2018/0281627 A1* | 10/2018 | Ali | B60N 2/2872 |

FOREIGN PATENT DOCUMENTS

| | | |
|---|---|---|
| CN | 205661405 U | 10/2016 |
| CN | 106344028 A | 1/2017 |
| CN | 106846725 A | 6/2017 |
| CN | 206414417 U | 8/2017 |
| CN | 107481476 A | 12/2017 |
| WO | WO-2016128478 A1 | 8/2016 |
| WO | WO-2017042286 A1 | 3/2017 |
| WO | WO-2019086599 A1 | 5/2019 |

OTHER PUBLICATIONS

"Chinese Application No. 201880083437.2, Office Action dated Jun. 3, 2021", (Jun. 3, 2021), 15 pgs.

"International Application PCT/EP2018/079993, International Preliminary Report on Patentability dated May 14, 2020", 11 pgs.

"Japanese Application No. 2020-524239, Notice of Reasons for Refusal dated Sep. 20, 2022", (Sep. 20, 2022), 16 pgs.

"Chinese Application No. 201880083437.2, Rejection Decision dated Oct. 9, 2022", (Oct. 9, 2022), 8 pgs.

* cited by examiner

CHILD SAFETY SEAT CHECKING SYSTEM, AND CHILD SAFETY SEAT CHECKING METHOD

PRIORITY CLAIM TO RELATED APPLICATIONS

This application is a U.S. national stage filing under 35 U.S.C. § 371 from International Application No. PCT/EP2018/079993, filed on 2 Nov. 2018, and published as WO2019/086599 on 9 May 2019, which claims the benefit under 35 U.S.C. 119 to German Application No. 20 2017 106 647.9, filed on 3 Nov. 2017, the benefit of priority of each of which is claimed herein, and which applications and publication are hereby incorporated herein by reference in their entirety.

The invention concerns a child seat checking system and a child seat checking method.

From US 2017/0021800 A1, a vehicle child seat is known, which includes a device that records and outputs a status of a restraint system of the child seat. Furthermore, a control device is discussed which can be connected to the OBD-II port of the vehicle and detects the status of a vehicle ignition. If the ignition is switched off and the restraint system indicates a status which indicates that a child is in the child seat, an alarm signal is generated after a predetermined period of time. The reliability and informative value of alarm signals generated according to this state of the art is considered to be in need of improvement.

It is therefore the object of the invention to propose a child seat checking system and a corresponding child seat checking method, wherein the risk of a child being left unintentionally in the vehicle is to be reduced in a reliable manner, wherein in particular false alarms should be avoided or the probability thereof should be at least reduced. Furthermore, in particular, the variability of the checking should be improved. Preferably, it should be possible, at least under certain circumstances, to leave the child deliberately behind, in the vehicle, without causing major inconvenience to the user of the checking system.

This object is solved with regard to a child seat checking system by the features of claim 1. Furthermore, the object is solved by the features of further independent claims, in particular concerning a child seat checking system, a computer-readable storage medium and a mobile device.

In particular, the object is solved by a child seat checking system comprising at least one child seat and a first checking device for checking whether a child is in the child seat and a second checking device for checking whether a person caring for the child is present.

In particular, a checking device is understood to be a device which, on the basis of a measurement (e.g. its own) or other input (e.g. a measurement by another device, in particular a sensor device), allows a determination to be made as to whether or not a certain condition or status (e.g. 'child in child seat' or 'caring person present') is present. This applies both to the first and second checking device, as mentioned here, and to subsequent (in particular the subsequent third and fourth) checking devices. Preferably, however, the respective checking devices include sensor devices which determine whether or not a condition or status is present by a measurement (in particular of a corresponding parameter). In particular, a checking device is also understood to mean a device (e.g. app) on a (mobile) device which can check whether or not a child is in the child seat (in the example of the first checking device) on the basis of a corresponding input (e.g. measurement of a sensor device external to the device). The (respective) checking device can be formed by only one assembly (e.g. defined by a housing) or be distributed over several assemblies (e.g. defined by several housings). Individual components, such as sensors, can be assigned to several checking devices.

According to a first preferred aspect of the invention, the second checking device is (at least partially) portable in an operating state of the child seat checking system. In particular, the second checking device can be at least partially formed by or be part of a mobile device (e.g. smartphone). A portable device is understood to be a device that can be carried (e.g. as a smartphone or as a component of a smartphone) by the person caring for the child. Various types of such mobile devices are discussed in more detail below. Such a checking device allows the presence of the person caring for the child to be easily and directly linked to the person (for example, if the person is carrying their smartphone). This makes the checking comparatively reliable. An operating state of the child seat checking system is a state of the system in which it is possible to check whether a child is in the child restraint or whether a person caring for the child is present. Hence, in particular, this check can be carried out when the second checking device is carried (in particular, not firmly attached to the vehicle). With an at least partially mobile second checking device it is not necessary, as described for example in US 2017/0021800 A1, to connect the second checking device to the vehicle electronics via the OBD II port. This port can sometimes be comparatively difficult to access.

Alternatively or additionally, the second checking device is designed to operate independently of an on/off state of the vehicle according to a second preferred aspect of the invention. By an on/off state it is particularly meant a state in which the ignition is either on (on-state) or off (ignition off). In particular according to the second aspect, a reliable alarm can be generated, wherein the probability of a false alarm is reduced. In particular, it has been recognized that coupling with an on/off state (ignition state) often results in a false alarm, as in some situations it is desired by the passengers of the vehicle to remain in the vehicle seats (while the child remains strapped in the child seat) while the ignition is off.

In general, the presence of a person caring for the child should preferably be understood to mean that the person caring for the child is in or (directly) next to the vehicle or, optionally, closer than a predetermined maximum distance from the child seat and/or vehicle. The maximum distance is preferably less than 50 m, in particular less than 25 m.

In accordance with a third preferred aspect (which is preferably combined with the first and/or second aspect), a third checking device is provided, the third checking device being designed to verify a status, in particular wakefulness status, of the child. By a status of the child it is meant a status which (directly) concerns the (present) child, such as in particular the question whether the child is awake or sleeping. It is also conceivable, for example, whether the child has an elevated body temperature or a normal one. The status of the child thus (directly) affects the physical constitution of the child. In particular, such a checking device can improve the ease of use of the child seat. For example, it is possible that a conscious decision to leave the vehicle (at least for a temporary period) may be made on the basis of a finding that the child is asleep, with the possibility, then, of returning to the vehicle immediately when the child wakes up by checking the child's sleep.

In accordance with a fourth preferred aspect of the invention (which may be combined in particular with the first and/or second and/or third aspect), a fourth checking device is proposed for checking a child seat environment, in particular a child seat ambient temperature. A checking of a child seat environment should in particular be a checking of air next to the child seat or a checking of the space volume in which the child seat is accommodated. A check of the ambient air temperature is particularly preferred. Optionally, it would also be conceivable that other parameters, such as air humidity and/or oxygen content and/or, optionally, harmful gases (such as carbon monoxide), could be checked alternatively or additionally.

First, second, third and/or fourth checking devices are preferably configured not only to perform the corresponding check but also to output or pass on a result of the check, in particular to a corresponding control device. In particular, the first, second, third and/or fourth checking device may comprise a (respective) output device for outputting a result of the check, in particular to one or more control devices, preferably of the above kind.

If a physical quantity is to be determined (e.g. force, weight, temperature and/or air humidity), corresponding measuring devices are preferably designed in such a way that at least four, preferably at least ten, from each other distinguishable measurement values can be measured. A (respective) optionally provided measuring device for measuring the temperature should preferably permit a temperature measurement which deviates from the actual temperature by a maximum of 2° C., preferably by a maximum of 0.5° C. and/or which covers a range of at least 5° C., possibly at least 20° C.

The third and/or fourth checking device is/are preferably provided (functionally and/or structurally) in addition to the first checking device. In particular, therefore, a check by the third and/or fourth checking device takes place separately (before, overlapping or after) from a check of the presence of the child. For example, information as to whether a child is in the child seat at all and information as to, for example, a child seat ambient temperature are provided separately. In this way, safety can be improved and a false alarm can be avoided optionally. In particular, the third and/or fourth checking device is not intended (only) to detect the presence of the child, but preferably to obtain further information concerning the child.

Preferably, at least one control device, in particular the one just mentioned, is provided, which is preferably configured to output, as a function of a check by the first, second, third and/or fourth checking device, at least one result from the respective check and/or at least one result from a comparison of several checks, in particular to an, preferably acoustic and/or optical, indicating device. The control device can, optionally, be arranged with the first, second, third and/or fourth, in particular with the first, third and fourth (e.g. in/on the child seat) or with the second (e.g. in/on a mobile device, in particular a smartphone) checking device, in a common assembly or a common housing, the housing preferably being formed by a mobile device (e.g. smartphone). Also the indicating device is optionally provided within the same or on the same housing as the control device and/or the first, second, third and/or fourth, in particular the second, checking device. The (respective) control device preferably comprises at least one (micro)processor and/or (micro)controller.

The child seat may have an electrical power supply (e.g. battery) and/or at least one connection for an electrical power supply and/or at least one connection for (wireless and/or wired) signal transmission.

Preferably, at least one, in particular acoustic and/or optical, indicating device is provided, which is configured to indicate, depending on a check by the first, second, third and/or fourth checking device, at least one result of the respective check or at least one result from a comparison of several checks. Preferably, the indicating device is configured to indicate all the results of the checks of the checking devices and/or to output an alarm signal if or when, respectively, an undesirable state with regard to the child and/or the presence of the caring person is detected (e.g.: child in child seat, caring person not present), in particular by comparing the check results, preferably taking into account all the check results of the (four) checking devices.

Preferably, at least one, in particular at least one of the above-mentioned indicating devices forms a structural unit (e.g. in the form of a smartphone) with the second checking device or at least parts thereof.

Alternatively or in addition, at least one, in particular at least one of the above, indicators may form a structural unit with the child seat.

An acoustic indication (output) means in particular a warning tone/warning signal and/or an acoustic message (voice message). An optical indication is understood in particular to be the lighting up of a light source (e.g. LED) and/or an indication on a display and/or an optical message (text message). As an alternative to an acoustic and/or optical indicating device, an indication (output) and/or an alarm can also be given by vibration or in some other way.

First, third and/or fourth checking device (or a corresponding first, third and/or fourth sensor device) may be arranged at least partially on and/or in the child seat, the fourth checking device (sensor device) preferably being arranged at least partially on an outer side of the child seat.

The second checking device should preferably (at least predominantly) be located outside the child seat. For example, only one transmitting and/or receiving device may also be located on and/or in the child seat in the case of the second checking device, for example when a mobile device (e.g. smartphone) determines its distance from the child seat. Alternatively, however, such a distance determination may also be carried out by a corresponding device in and/or on the child seat. In particular in the case of the second checking device, it may be provided that it is distributed over several locations (e.g. child seat and mobile device) in accordance with an embodiment and, ultimately, comprises transmitters/receivers which allow their distance to each other to be determined by means of joint communication (e.g. by signal attenuation due to an increased distance).

The first checking device should preferably comprise at least one restraint sensor configured to detect a status of at least one restraint, such as a safety belt and/or a body harness.

In addition, the first (and/or third) checking device may include at least one weight sensor (preferably in/on the child seat, for example on a seat element and/or the base in the case of child seats which may be made up of several parts), which reacts accordingly to a child in the child seat or its weight. A corresponding weight sensor can be arranged on or at a seat section and/or a backrest section of the child seat.

The first (and/or third) means of checking may, in embodiments, include at least one optical device, such as a (video) camera, which determines in particular whether a child is seated in the child seat or whether the child is moving. In particular, the (video) camera may be located in or on a carrying handle (carrying hanger) of the child seat.

In one configuration the restraint may include a belt system. In this case, the first checking device may include a sensor device which detects whether one or more (optionally all) of latching tongues are connected to a corresponding buckle. In a connected (locked) condition, an electrical circuit may be optionally closed (if all the belt tongues are connected to the corresponding buckle). In addition, a corresponding electrical circuit may be open if at least one belt tongue is not connected to a corresponding buckle. In such a checking device or sensor device, the (ohmic) resistance may be a suitable parameter for checking. In general, it is also possible to detect other physical (electromagnetic) parameters, such as a capacitance or the like. However, testing the resistance is preferred.

Furthermore, in the case where the restraint comprises a belt system, the first (and/or third) checking device may comprise a sensor to detect an (mechanical) action, preferably (tensile) tension, inclination, flexion and/or torsion, on one or more elements of the belt system (for example a shoulder belt, a lap belt, a buckle attachment, a chest strap, a chest clip, etc.). In this respect, reference is made in particular to WO 2017/042286 A1 with regard to the further design. Alternatively or additionally at least one Hall sensor can be used. Alternatively or additionally, other electrical properties such as resistance, capacitance and/or inductance can be measured (in this context, explicit reference is made to the disclosure according to WO 2016/128478 A1). The first checking device may also include a pressure sensor (alternatively or additionally) which detects the pressure at a suitable location of the belt system (which in turn may be regarded as an indirect measurement of belt tension).

In the case where the restraint comprises a (rigid) device such as an impact shield, the first (and/or third) checking device may include a pressure sensor which preferably rests on one side (surface) of the (rigid) restraint which is intended to come into contact with the child (sitting in the child seat).

The second checking device may include at least one on-board sensor, such as a weight sensor and/or ignition sensor. In particular, the weight sensor may be a sensor located on or in a seat (preferably the driver's seat) integrated in the vehicle. Alternatively or additionally, a (video) camera, for example, can be used as the vehicle's on-board sensor. Other alternatives are possible. In any case, preferably when using a vehicle's on-board sensor, a device is provided which allows a connection to the vehicle electronics, for example via an OBD II port (see also US 2017/0021800 A1 in this regard).

Alternatively or additionally, the second checking device may (at least partially) include an electronic (terminal) device for use by the caring person (e.g. smartphone, smartwatch, separate checking device or similar). In this case, a distance between the child seat and the electronic (terminal) device can preferably be used (as a direct or indirect) signal for the presence of the caring person.

In embodiments, the second checking device may comprise a mobile (terminal) device, such as a mobile telephone, in particular a smartphone, and/or a watch, in particular a Smartwatch, and/or an activity tracker and/or a visual and/or hearing aid and/or an ignition key, in particular an electric or electronic one, and/or another mobile device, in particular comprising a transmitter and/or receiver and/or transponder. Any mobile device may be equipped with a (optionally also mechanical) key connection device to enable a (optionally mechanical) connection with the (optionally electrical or electronic) vehicle key. A visual and/or hearing aid can also be understood to be devices which do not necessarily (but optionally) improve "seeing" or "hearing", for example to compensate for a visual and/or hearing defect, but also devices which supply additional information (e.g. an "augmented reality" or extended reality, which means in particular a computer-aided extension of the perception of reality, e.g. "Google Glass™") to the respective sensory organ. Alternatively or additionally, a distance determination device may be provided as a second checking device (or part of such a device), which may be located outside of (a) mobile device(s), e.g. on/in the child seat, and which is configured to determine a distance between the child seat and (a) mobile device(s), such as a mobile telephone, in particular a smartphone, and/or a watch, in particular a Smartwatch, and/or an activity tracker and/or a visual and/or hearing aid and/or an ignition key, in particular an electric or electronic one, and/or another mobile device, in particular comprising a transmitter and/or receiver and/or transponder.

A mobile device may include devices for acoustic and/or visual and/or haptic (in particular by vibration) signaling of a status of the child seat, in particular appropriate means for signaling an undesirable constellation regarding the status of the child by alarm. Furthermore, such a mobile (electronic) device may allow the user to suppress the alarm, for example for a predetermined period of time. If the mobile device is a smart device (e.g. smartphone, smartwatch or similar), such functionalities can be implemented by a corresponding app.

The third checking device preferably comprises at least one motion sensor and/or camera and/or noise sensor and/or at least one weight sensor and/or at least one sensor for determining a physical condition of the child, such as a pulse sensor and/or a respiration sensor. If the third checking device comprises a motion sensor, a sensor device (also) associated with the first checking device can be used for this purpose, as explained above. The third checking device may also include a weight sensor, as explained in relation to the first checking device. In general, a sensor associated with the third checking device is preferably configured to measure with such accuracy that a distinction can be made between, on the one hand, a calm (in particular sleeping) child, which is at least substantially motionless or moves regularly, and, on the other hand, an awake child, in particular one moving aperiodically, or even a startled or angry child, in particular one moving jerkily and irregularly.

One and the same video camera can also be used to determine both the presence of the child in the context of the first checking device and its activity (i.e. whether it is asleep or awake) in the case of the third review facility.

The fourth checking device may include at least one thermometer allowing to determine the temperature inside the vehicle, close to the child in the child seat. Alternatively or in addition, the fourth checking device may include a humidity sensor and/or a gas sensor (in particular to detect noxious gases such as carbon monoxide).

The first, second, third and/or fourth checking device (individually) may comprise several sensors and/or a sensor array.

Preferably, the child seat and the second checking device may be designed for wireless communication via a first wireless communication link, e.g. Bluetooth. A measurement, e.g. distance measurement, based on the first communication link may preferably be communicated via the first communication link or a second wireless communication link, e.g. a mobile radio network link. Alternatively or additionally, if the first wireless communication link is interrupted, corresponding information, in particular a corresponding alarm, can be generated or output, preferably automatically (analogous to a baby monitor) or by communicating via the second wireless communication link. Preferably the second wireless communication link has a greater range (in particular by at least a factor of two, preferably at least a factor of 10) than the first wireless communication link. The first wireless communication link may have a range of less than 100 m or less than 50 m. The second wireless communication link may have a range of more than 100 m or more than 10 km or a (substantially) global range.

Several of the first, second, third and fourth verifying devices may have a common sensor device (such as a common weight sensor, a common sensor of a restraint and/or a common camera). Examples of such common sensor devices have been explained above.

First, second, third and/or fourth checking device and/or control device and/or indicating device can be designed for wireless communication (with each other), in particular via radio and/or Bluetooth and/or infrared, and/or for Internet-based communication. This further simplifies the checking process.

Preferably, the presence of the caring person is determined or estimated by evaluating communication between the child seat or vehicle in which the child seat is located and a mobile device (e.g. smartphone).

Any measurement result from sensor devices used can be output to one (the above) or more control device(s) and be (especially there) compared with corresponding reference values. Depending on the result of such a comparison, the control device(s) can determine whether:
- a child is in a child seat or not,
- a caregiver is present (or removed)
- the child is sleeping or awake, and/or
- the external environment (especially temperature) in the vehicle is appropriate for the child or not.

Furthermore, the above-mentioned object shall be solved by a child seat checking method, preferably using a child seat checking system as described above, comprising:
a) Checking whether a child is in a child seat; and
b) Checking whether a person caring for the child is present.

According to a first preferred aspect of the child seat checking method, step (a) is carried out by means of a checking device which is (also during checking) portable (i.e. not necessarily connected to the vehicle, in particular an OBD II port, especially during checking).

In accordance with a second preferred aspect of the child seat checking method (as an alternative or in addition to the first preferred aspect), it is proposed that a checking device in step (b) is used which is designed to operate independently of the operating condition of the vehicle or which operates independently of the operating condition of the vehicle (during checking).

According to a third preferred aspect of the child seat checking method (which can preferably be combined with the first and/or second aspect), the checking of a status, in particular wakefulness status, of the child is proposed.

According to a fourth preferred aspect of the child seat checking methos (which may be combined in particular with the first, second and/or third preferred aspect of the child seat review process), it is proposed to review a child seat environment, in particular a child seat ambient temperature.

Preferably, a visual and/or audible indication, in particular a visual and/or audible alarm, is given, in particular without any further conditions having to be met, preferably immediately, if (where KiKS=child in child seat, Ba=caring person present, Kw=child awake, TiaB=temperature in acceptable range):
KiKS=yes, (Ba=any,) (Kw=any,) TiaB=no; and/or
KiKS=yes, Ba=no, possibly Kw=yes, (TiaB=any).

Alternatively or additionally, a visual and/or audible indication, in particular a visual and/or audible alarm, may not be given or (only) be given when preferably a predetermined time has elapsed, and if:
KiKS=yes, Ba=no, possibly Kw=no, (TiaB=any).

A (visual and/or audible) indication, in particular a (visual and/or audible) alarm, preferably does not occur (in particular not even after a certain time has elapsed) if:
KiKS=no, (Ba=any,) (Kw=any,) (TiaB=any); and/or
KiKS=yes, Ba=yes, (Kw=any,) if necessary TiaB=yes; and/or
the indication or alarm is suppressed by the caring person, which is preferably possible at least for a period of time t1, in particular when Ba=no and/or Kw=yes, or when the child wakes up and/or, which is preferably not possible or only for a temporary period of time t2, preferably less than t1, possible, if the temperature is not within an acceptable range.

In a preferred version of the child seat checking method, a change of status from child=awake to child=sleeping only occurs when the caring person is present. So even if the child falls asleep, the status of child=wake is still maintained (the child is considered awake) if the caring person is not present.

The above-mentioned object is further solved by a computer-readable storage medium, in particular of a mobile device (e.g. smartphones), which contains instructions that cause at least one processor to perform a child seat checking method of the above type when the instructions are executed by at least one processor.

The above-mentioned object is further solved by a mobile device configured to perform the above child seat checking method and/or comprising (at least partially) a child seat checking system of the above-mentioned type.

The child seat can be a baby carrier or a (classic) child seat for older children. In any case, the child seat is preferably designed to be removable from the vehicle in/on which it is to be installed. The child seat may have a base (i.e. may comprise a seat element and a base).

In particular, the child seat is a child seat for a motor vehicle (passenger car and/or truck).

The above-mentioned object is further solved independently by a vehicle, in particular a motor vehicle, more preferably a motor vehicle (in particular a passenger car or a truck) comprising a child seat checking system of the above-mentioned type. The above-mentioned object is further solved by such a vehicle together with at least one mobile device (e.g. smartphone). A corresponding child seat is, then, preferably mounted on such a vehicle.

Further features result from the sub-claims.

Figure 2:
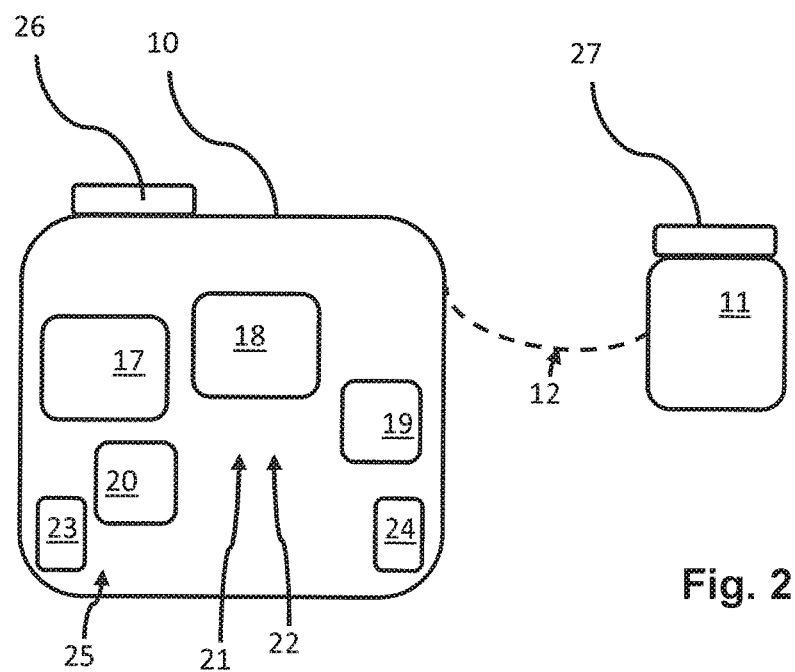

In the following, the invention is explained in more detail by means of embodiments. In this connection show:

FIG. 1 an oblique view of a child seat checking system according to the invention (partly in oblique view, partly schematic);

FIG. 2 a schematic child seat checking system according to the invention with further details.

In the following description, the same reference numbers are used for parts that are identical and have the same effect.

FIG. 1 shows a child seat 10 (in oblique view) and a second checking device (e.g. in the form of or formed by a smartphone) 11. The second checking device 11 can communicate wirelessly with the child seat 10 (or components thereof) via a path 12.

The child seat 10 has a belt system 13. A tension sensor (e.g. comprising an elastic element which changes its (electrical) resistance when it is stretched due to an applied tension force) is in shoulder belts 14, 15. In this context, tension is always understood to mean mechanical tension, unless otherwise specified.

The (respective) voltage sensor preferably measures at intervals of 1 to 1000 milliseconds, e.g. 100 milliseconds, and is connected to a control unit 17 (see FIG. 2). Part of the control device 17 (or assigned to it) is a power supply 18 (e.g. battery) and a signal transmission device 19.

The control unit 17 calculates preferably every 1 to 100, e.g. every 10 seconds, an average value and if necessary a standard deviation of the measured voltage values.

The voltage sensor 20, together with the control device 17, the power supply 18 and the signal transmission device 19, is part of a first checking device 21 and a third checking device 22.

The child seat 10 further comprises, in particular two, (resistance) thermometers 23, 24. One of the thermometers 23, 24, respectively, may be located on one side of the child seat 10, preferably on a respective lateral outer surface of the child seat 10 (in particular in an area corresponding to the head or shoulder area of the child in the child seat). The respective thermometer 23, 24 measures the temperature of the ambient air every 1 to 1000, e.g. every 100, milliseconds. Furthermore, the thermometers 23, 24 are connected to the control device 17 and the signal transmission device 19. The control unit 17 calculates an average of the measured temperatures every 1 to 100, e.g. every 10 seconds. The thermometer(s), the control unit 17, the power supply 18 and the signal transmitter 19 are part of a fourth checking device 25.

The second checking device 11 is preferably formed (at least partly formed) by a mobile device (in particular a smartphone), wherein the smartphone can preferably have a corresponding software (app). An assignment between a specific child seat and a specific second checking device 11 (smartphone) can be carried out by a basically known method, wherein each child seat can be assigned to one or more second checking devices 11 and/or each second checking device (smartphone) can be assigned to one or more child seats.

If the child seat changes its status regarding the presence of the child (from "free" to "occupied"), a (Bluetooth) connection can be established between the child seat and the associated smartphone, optionally. If no connection can be established (for example, within a predetermined time, from 1 to 50 in particular, e.g. 5 seconds), the child seat can emit an alarm (e.g. an acoustic alarm) which may not be suppressed. As long as at least one associated smartphone is in a (Bluetooth) connection with the child seat, the child seat will preferably not send any data from the respective sensors to the second checking device 11 (smartphone). If the temperature falls below a predetermined lower limit value (of for example 10° C. or less) and/or rises above a predetermined upper limit value (of for example at least 30° C. or at least 35° C. or more), in particular while the (Bluetooth) connection is maintained, the child seat can transmit an (in particular acoustic) alarm, which can be suppressed optionally (directly) at the child seat and/or via the second checking device 11 (smartphone) once for 2 to 20, in particular 10, minutes.

If the (Bluetooth) connection is interrupted while the temperature is (still) too low or too high, the signal transmitting device 19 may, optionally, after a predetermined time (of, for example, at least 20 seconds or at least 30 seconds or more) send the calculated average temperature to the second checking device 11 (smartphone) via mobile connection (here and in the following: preferably mobile network connection), which may cause the second checking device 11 (smartphone) to emit an alarm (acoustic and/or visual and/or vibratory). This alarm may be suppressed for a certain period of time (for example, 1 to 5 minutes, preferably 2 minutes).

As long as no presence of a child in the child seat is detected, preferably no (Bluetooth) connection is established between the child seat and the second checking device 11 (smartphone) and the child seat 10 then sends in particular no data to the second checking device 11 (smartphone).

If the child seat is occupied (i.e. a child is present) by a sleeping child (which can be determined in particular by the information provided by the voltage sensors, in particular in that the average measured voltage exceeds a first predetermined threshold value while the standard deviation remains below a second predetermined threshold value), and the (Bluetooth) connection is interrupted while the temperature is (still) in an acceptable range (z. e.g. within 10 to 35° C.), the signal transmitting device 19 can signal after a predetermined time (of e.g. 1 to 5, in particular 2, minutes) to transmit the last calculated information from (all) participating sensor devices to the second checking device 11 (smartphone) via mobile connection, so that the second checking device 11 (smartphone) emits an acoustic and/or visual and/or vibratory alarm. This alarm can be suppressed once or several times (for example three times) for a certain time (for example 5 to 20, in particular 10 minutes, as a total of 30 minutes, optionally).

If the child seat is occupied by an awake child and the (Bluetooth) connection is interrupted while the temperature is still within an acceptable range, the signal transmitting device 19 of the child seat 10 may transmit after a predetermined time (e.g. 10 to 100, in particular 30 seconds) the last calculated information from (all) corresponding sensors of the child seat 10 to the second checking device 11 (smartphone) via mobile connection, so that the second checking device 11 (smartphone) is caused to emit an acoustic and/or visual and/or vibratory alarm. This alarm can be suppressed once (or several times) for a certain time (for example 5 to 20, especially 10 minutes), optionally.

If no signal has been sent or has not yet been sent and the temperature falls outside the permitted range and/or the child wakes up, the signal transmitting device 19 of the child seat 10 can send after a predetermined time (of for example 1 to 100, in particular 30, seconds) the last calculated information from (all) sensor devices of the child seat 10 to the second checking device 11 (smartphone) via mobile connection, so that the second checking device 11 (smartphone) is caused to emit an acoustic and/or visual and/or vibratory alarm. This alarm can be suppressed once (or alternatively several times) for a predetermined time (of for example 1 to 5, in particular 2, minutes) (if it is caused by the temperature) or can be suppressed for a further, in particular deviating, predetermined time of for example 5 to 20, in particular 10, minutes (if it is caused by the child waking up). Preferably the alarm will not stop when the child's status returns to "sleeping" and/or when the temperature returns to an acceptable range.

In general, when the child seat 10 sends data via a mobile connection to the second checking device 11 (smartphone), it may preferably send this data to the last (Bluetooth) connected checking device 11 (smartphone) (or a plurality of second checking devices 11 or smartphones, if several checking devices 11 or smartphones have lost their (Bluetooth) connection to the child seat 10, in particular within a certain time period of, for example, 2 to 10, in particular 5 minutes).

Any alarm issued by the second checking device 11 (smartphone) may preferably end automatically as soon as a (Bluetooth) connection between the child seat and an associated second checking device 11 (smartphone) is re-established. Apart from this, it is possible to switch off the entire system directly at the seat (but preferably not via the second checking device 11 or the smartphone), which terminates all alarms (including those that cannot be suppressed in principle, at least via the second checking device 11 or the smartphone). Before switching off, a message is then preferably sent to all assigned second checking device 11 (smartphones) via mobile connection.

An alarm (if not excluded) can be suppressed by the second checking device 11 (smartphone) or directly on the child seat. If it is done directly at the child seat, a corresponding message is preferably sent to all assigned second checking devices 11 (smartphones) via mobile connection.

The control device 17 can also be formed (partially or completely) by the second checking device 11 (or smartphone).

The child seat preferably has an indicating device 26 (in particular a display). Alternatively or in addition, the second control device may also have an indicating device 27 (in particular a display).

When confronted with the following situations, the control device can react as follows:

| Child seat occupied (KiKS)? | Caring person present (Ba)? | Child awake (Kw)? | Temperature OK (TiaB)? | Alarm |
|---|---|---|---|---|
| No | Any | Any | Any | No alarm |
| Yes | Any | Any | No | Alarm |
| Yes | Yes | Any | Yes | No alarm |
| Yes | No | Yes | Yes | Alarm |
| Yes | No | No | Yes | No alarm |

The above rules can be modified and/or completed. In preferred embodiments, one or more of the following rules can be followed (by the control device):

- An alarm is never triggered if there is no child in the child seat.
- An alarm is always triggered if a child is in the child seat and the temperature is too high or too low.
- An alarm is always triggered when a child is in the child seat, the child is awake and no caring person is present.
- An alarm is triggered after a predetermined period of time if a child is in the child seat and the child is sleeping and no caring person is present.
- An alarm cannot be suppressed (or only for a time, especially for a comparatively short time) if it is triggered by a temperature status.
- An alarm cannot be suppressed for a predetermined period of time if it is caused by the absence of a caring person and/or by the child waking up.
- The child's status can only change from "awake" to "asleep" if a caring person present.

It should be noted at this point that all the parts described above, taken individually and in any combination, in particular the details shown in the drawings, are claimed to be inventive. Modifications of this are familiar to the person skilled in the art.

Reference Signs
10 Child seat
11 Second checking device
12 Path
13 Belt system
14 Shoulder strap
15 Shoulder strap
17 Control device
18 Energy supply
19 Signal transmitting device
20 Voltage sensor
21 First checking device
22 Third checking device
23 Thermometer
24 Thermometer
25 Fourth checking device
26 Indicating device
27 Indicating device

The invention claimed is:

1. A child seat checking system for a child seat of a motor vehicle, the system comprising:
   at least one child seat;
   a first checking device for checking whether a child is in the at least one child seat;
   a second checking device for checking whether a person caring for the child is present, wherein the second checking device is at least partially portable and is configured to operate independent of a state of the vehicle;
   a third checking device, wherein the third checking device is configured to check a wakefulness status of the child; and
   a controller coupled to the first checking device, the second checking device, and the third checking device, the controller configured to check whether a child is in the at least one child seat and wherein the controller is configured to check whether a person caring for the child is present, and wherein the controller is configured to check a wakefulness status of the child, and wherein a change of status from child awake to child sleeping only occurs when the caring person is present.

2. The child seat checking system according to claim 1, further comprising:
   a fourth checking device coupled to the controller, wherein the fourth checking device is configured to check an ambient temperature.

3. The child seat checking system according to claim 2, further wherein the controller is configured to output at least one result to an acoustical indicating device or an optical indicating device, the at least one result derived from the first, the second, the third, or the fourth checking device, or the at least one result corresponding to a comparison of the first, the second, the third, or the fourth checking device.

4. The child seat checking system according to claim 3 wherein the first checking device, the second checking device, the third checking device, the fourth checking device, or the controller, or the acoustical indicating device, or the optical indicating device is configured for wireless communication via radio, Bluetooth, infrared, or Internet.

5. The child seat checking system according to claim 3 wherein the at least one child seat and the second checking device are configured for wireless communication via a first wireless communication link, wherein a measurement based on the first communication link is communicated via the first communication link or via a second wireless communication link or, wherein if the first wireless communication link is interrupted, then an alarm is generated automatically or by communicating using the second wireless communication link.

6. The child seat checking system according to claim 2 wherein at least one of the first, the second, the third, or the fourth checking device comprises an output means for outputting a result of the checking to one or more control devices.

7. The child seat checking system according to claim 2 further comprising:
at least one indicating device having an acoustical or optical output, the at least one indicating device structurally integrated with the second checking device and configured to indicate an alarm signal upon detecting an undesirable condition corresponding to the child or the person caring for the child.

8. The child seat checking system according to claim 2 wherein the first, third or fourth checking devices are at least partially on or in the at least one child seat or the fourth checking device is at least partially on an outer side of the at least one child seat.

9. The child seat checking system according claim 2 wherein:
the first checking device comprises:
at least one restraint device sensor configured to determine a status of at least one restraint device, the restraint device including a retaining belt or an impact shield, or at least one weight sensor, or at least one optical camera,
the second checking device comprises:
at least one on-board sensor, the on-board sensor including a weight sensor or an ignition sensor, or
a mobile device, the mobile device including a telephone, a watch, a Smartwatch, an activity tracker, a visual aid, a hearing aid, an ignition key, a transmitter, a receiver, or transponder, or a distance determining device configured to determine a distance between the at least one child seat and the mobile device, and
the third checking device comprises:
at least one motion sensor, a camera, a noise sensor, or at least one weight sensor, or at least one sensor for determining a physical condition of the child, wherein the at least one sensor for determining a physical condition includes a pulse sensor or a respiration sensor.

10. The child seat checking system according to claim 2 wherein the first checking device, the second checking device, the third checking device, or the fourth checking device includes a plurality of sensors or a sensor array.

11. A child seat checking method comprising:
using a controller to check whether a child is in a child seat; and
using the controller to check whether a person caring for the child is present, and wherein the controller is coupled to a checking device configured to be portable and to operate independently of the operating state of vehicle in which the child seat is attached,
wherein the controller is configured to check a wakefulness status of the child,
wherein a visual indication or audible indication is given upon one or both of
discerning a first condition in which a child is in the child seat and an environmental temperature is not in an acceptable range, and discerning a second condition in which the child is in the child seat and the caring person is not present;
or the visual indication or audible indication is not given, or only occurs when a predetermined time has elapsed, upon discerning a third condition in which the child is in the child seat, and the caring person is not present, and the child is not awake, and the temperature is in an acceptable range;
or the visual indication or the audible indication is not given
upon one or several of
discerning a fourth condition in which the child is not in the child seat, and
discerning a fifth condition in which the child is in the child seat and the caring person is present; and
when the indication or alarm is suppressed by the caring person, for a period of time of at least t1 when the caring person is not present, which is only possible for a temporary period of time t2 if the temperature is not within an acceptable range, wherein t2 is less than t1; and
wherein a change of status from child awake to child sleeping only occurs when the caring person is present.

12. The seat checking method according to claim 11, wherein the controller is configured to check the child seat environmental temperature.

13. A non-transitory computer-readable storage medium configured for execution on a mobile device, the storage medium having instructions configured to execute the child seat checking method according to claim 11.

14. A mobile device configured to perform the child seat checking method according to claim 11.

15. The child seat checking method according to claim 11, wherein the wakefulness status is checked by a checking device coupled to the controller, and wherein the checking device is configured to measure with such accuracy that a distinction can be made between a calm child and a moving child.

16. A child seat checking method comprising:
using a controller to check whether a child is in a child seat; and
using the controller to check whether a person caring for the child is present, and wherein the controller is coupled to a checking device configured to be portable and to operate independently of the operating state of vehicle in which the child seat is attached,
wherein the controller is configured to check a wakefulness status of the child,
wherein a change of status from child awake to child sleeping only occurs when the caring person is present.

* * * * *